United States Patent [19]

Horton et al.

[11] Patent Number: 4,576,311
[45] Date of Patent: Mar. 18, 1986

[54] TAB DISPENSER WITH ODOR APPLICATOR

[76] Inventors: Stuart L. Horton, 9 Woodward Rd., Cromer, New South Wales 2099; Frederick P. Kann, 2/6 Elizabeth Parade, Lane Cove, New South Wales 2066, both of Australia

[21] Appl. No.: 527,793
[22] Filed: Aug. 30, 1983
[51] Int. Cl.[4] .................. B65D 83/08; B65H 5/28
[52] U.S. Cl. ..................... 221/73; 221/135; 118/235; 118/264; 156/584; 156/DIG. 48; 206/447; 242/55; 428/905
[58] Field of Search .................. 221/69–74, 221/46, 135, 197; 156/523, 575, 577, 584, DIG. 48, DIG. 50; 242/55; 118/235, 264; 222/187, 190; 206/447, 820; 428/905, 42

[56] References Cited

U.S. PATENT DOCUMENTS

| 2,737,149 | 3/1956 | Collins, Jr. et al. | 118/264 X |
| 3,066,881 | 12/1962 | Krueger | 221/73 X |
| 3,494,505 | 2/1970 | Huebner | 222/107 X |
| 3,740,299 | 6/1973 | Schroter et al. | 156/577 |
| 3,748,211 | 7/1973 | Hoopengardner | 156/575 |
| 4,199,392 | 4/1980 | Hamisch, Jr. | 156/DIG. 48 X |
| 4,277,024 | 7/1981 | Spector | 428/905 X |

FOREIGN PATENT DOCUMENTS

| 842909 | 6/1939 | France | 221/73 |
| 52-11997 | 1/1977 | Japan | 221/73 |
| 677070 | 8/1952 | United Kingdom | 221/73 |
| 1329309 | 9/1973 | United Kingdom | 428/905 |

Primary Examiner—Joseph J. Rolla
Assistant Examiner—Kevin P. Shaver
Attorney, Agent, or Firm—Ladas & Parry

[57] ABSTRACT

A dispensing device for perfumes or deodorants comprises a housing for a reel of mounting tape with tabs adhesively mounted thereon. The mounting tape extends to a member impregnated with the perfume or deodorant and is passed against the member for coating the upper tab surface. The mounting tape extends to and around a discharge member for redirecting the mounting tape through a sharp angle and to dispense the coated tabs through a discharge opening in the housing. A take-up reel is provided for winding the mounting tape. A thumb wheel moves the take-up reel and operates the dispenser.

6 Claims, 5 Drawing Figures

TAB DISPENSER WITH ODOR APPLICATOR

FIELD OF THE INVENTION

This invention relates to dispenser devices, for perfumes, deodorants and like substances which emit an odor or smell. Such substances will herein be referred to as "substances of the kind described".

BACKGROUND OF THE INVENTION

The common methods of dispensing and applying deodorants or perfumes are by hand from a bottle, using an aerosol can or roll-on type container (a container having a rotatable ball at one end by which means liquid is applied). The problem with all these methods of application is that it is necessary to apply liquid or powder directly to the skin, which can lead to skin diseases. Additionally, the perfume or deodorant, may be harmful to the fabric of clothes that it may contact.

It is an object of the present invention to provide a compact and inexpensive dispenser device for perfumes, deodorants or other substances of the kind described, by use of which perfume does not require application directly to the skin.

SUMMARY OF THE INVENTION

Accordingly this invention provides a dispenser device having a housing, a supply reel within the housing incorporating a mounting tape and a series of tabs releasably and adhesively mounted on the mounting tape, the mounting tape extending from the supply reel to an applicator containing perfume or deodorant and being arranged to apply a coating of the perfume or deodorant to the top surface of the tabs, the mounting tape extending from the applicator to discharge means arranged such that the mounting tape is sharply redirected adjacent a discharge opening, the mounting tape extending from the discharge opening to a take-up reel, the arrangement being such that in use as the mounting tape is sharply redirected adjacent the discharge opening, a tab having its top surface coated with perfume or deodorant is released from the mounting tape and is discharged from the discharge opening, the mounting tape from which tabs have been released being taken up by the take-up reel.

In accordance with the invention, tabs are discharged from the discharge opening having a top surface coated with a substance of the kind described, which may be a perfume or deodorant. The tab may then be applied by means of adhesive remaining on its bottom surface to any convenient position for example a collar or lapel so that the substance can perform its function without requiring direct application to the skin. Further, direct contact of the substance on the tab with the fabric of clothes is avoided since the tab forms a barrier between the perfume and the fabric to which the tab is attached.

A further advantage of employing a dispenser in accordance with the present invention as compared with prior methods of applying perfume or deodoriser, is that it is very economic in the amount of perfume it uses. Further, the dispenser device according to the present invention can be constructed compactly and inexpensively.

Where the tab carries a deodoriser for treating air, it may for example be applied to the mouth-piece of a telephone handset or other sensitive area.

Since the mounting tape is taken up by take-up means after dispensing tabs, it is unnecessary to dispose of waste material in the form of torn off parts of mounting tape.

The tabs may be formed of paper, plastics film or aluminium foil.

The dispenser device is preferably constructed so as to be re-usable, that is the housing may be opened so that a new supply reel may be mounted within the housing. Further, the means for applying a liquid or viscous substance may be formed as a replaceable insert so that when the liquid or viscous substance is exhausted, a new insert may be positioned within the housing. To this end the insert may have a snap-fit mounting. Alternatively a number of inserts may be supplied with the dispenser device so that a variety of perfumes may be used.

The means for moving the mounting tape is preferably a manually operable means, for example a thumb wheel. The thumb wheel may be integral with a take-up reel. As an alternative to a take-up reel, the take-up means may comprise a stuffing box into which the mounting tape is fed by a suitable tape gripping means.

DESCRIPTION OF THE DRAWINGS

A preferred embodiment of the invention will now be described with reference to the accompanying drawings wherein.

DESCRIPTION OF PREFERRED EMBODIMENT

Figure 1:
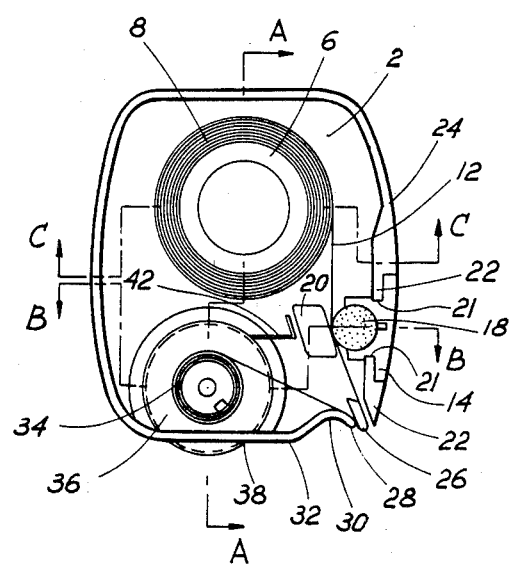
FIG. 1 is a plan view of a dispenser device according to the invention with lid removed.

Referring to the drawings, the dispenser device according to the invention comprises a 2-part housing having a base part 2 and a lid part 4.

The housing base 2 has a circular upstanding hub 6 which serves as the spool for a reel 8 of mounting tape. The lid part 4 has a circular portion 10 which fits closely within spool 6 in order to locate the lid part on the base part.

Figure 5:
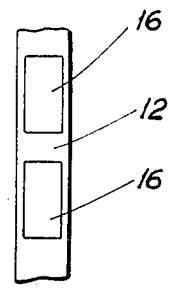
FIG. 5 is an elevational view of a mounting tape carrying tabs.

Mounting tape 12 is led from the reel of mounting tape 8 mounted on spool 10 towards an applicator insert 14. The mounting tape is shown in elevation in FIG. 5 and comprises a series of rectangular tabs 16 adhesively mounted at predetermined positions on the mounting tape 12. The mounting tape is a well known commercially available tape, and the tabs can be removed by peeling from the mounting tape.

The applicator insert 14 comprises a member 18 formed of felt, paper or other porous material impregnated with a substance which it is desired to apply as a coating to the tabs 16.

The applicator felt 18 is mounted in a semi-circular recess in insert 14 and is positioned so as to bear the mounting tape 12 against a generally rectangular back stop 20, back stop 20 being formed integral with base member 2. Applicator insert 14 is formed as a replaceable insert and has recesses 21 in its sidewalls which make a snap fit engagement with projecting portions 22 of a top sidewall 24 of base plate 2.

As an alternative to the above impregnated porous member, a roll-device may be used comprising a cartridge of liquid having at one end a rotatable ball which applies the liquid to the tape 16.

Figure 2:
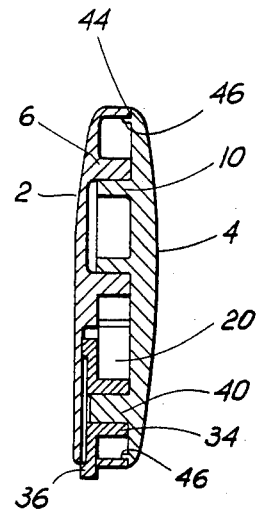
FIG. 2 is a sectional view along the line AA of FIG. 1.
Figure 3:
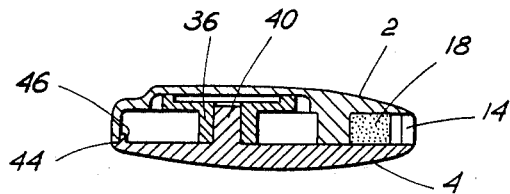
FIG. 3 is a sectional view along the line BB of FIG. 1.
Figure 4:
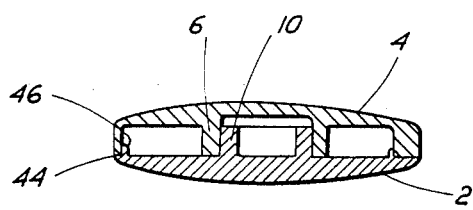
FIG. 4 is a sectional view along the line CC of FIG. 1.

The mounting tape 8 after passing by the applicator 14 is positioned over an elongate discharge member 26 mounted within a discharge opening 28. The mounting tape subtends a large obtuse angle of about 160 degrees as it moves over the discharge member 26. The mounting tape makes contact with an inwardly contoured portion 30 of a sidewall 32 of base plate member 2. After passing over contoured portion 30, the tape is wound on a take-up reel 34. The take-up reel 34 is integral with a thumb wheel 36 which projects through an opening 38 in sidewall 32 so that the thumb wheel can be operated manually. The thumb wheel and take-up reel are held in position by a stem 40 (FIGS. 2,3) which projects downwardly from cover plate 4. A non-return ratchet device 42 comprising a leaf spring is mounted so as to engage the milled surface of the thumb wheel 38 at an acute angle to the anti-clockwise movement of the thumb wheel, as seen from FIG. 1. This non-return ratchet device prevents clockwise movement of the thumb wheel 34 which would act to unwind the mounting tape from the take-up roll. A bead 44 projecting from the top inner surface of base walls 24, 32 is engaged by a complementary recess 46 which runs along the inside edge of cover member 4 so as to make a snap fit of the two parts of the housing.

In use of the dispenser device, the device which is shown as two times lifesize scale, is held in the palm of the hand and the thumb wheel is moved in an anti-clockwise direction. This has the effect of winding the mounting tape 12 upon the take-up reel 34, and this causes the mounting tape to be unwound from the mounting reel 8 and moved between the applicator 14 and the backup member (unnumbered). This causes a coating of liquid or viscous material to be applied to the tabs 16 on the mounting tape and further movement of the thumb wheel causes the tab 16 coated with perfume or deodoriser to be ejected from the discharge opening as the mounting tape moves through a sharp angle over the discharge member 26, the forces arising through the bending of the mounting tape overcoming the forces of adhesion of the tab 16 to the mounting tape. The tabs 16 are positioned on the mounting tape having as a minimum distance therebetween the distance between the applicator 14 and the discharge member 26; this is to prevent tabs being coated and then being left in the intermediate region between applicator 14 and the discharge opening. As an additional measure to ensure that only the minimum amount of liquid is ejected from the applicator, the mounting tape may be formed of a moisture repellent substance so as to ensure that mounting tape does not absorb liquid or viscous substances.

When a tab has been dispensed from the dispenser, the tab may be applied with finger pressure to any desired spot, as for example a collar or lapel. The adhesive on the rear of the tab serving to hold the tab to the point of application.

There has thus been described a compact and inexpensive dispenser for substances of the kind described such as perfumes or deodorants.

The applicator inserts within the dispenser device may be interchanged for varying requirements and spare liquid applicators may be supplied for this purpose, either with or without liquid impregnation. The dispenser is reusable and can be filled with tabs and applicator inserts.

We claim:

1. A dispenser device having a housing with a discharge opening, a supply reel within the housing incorporating a mounting tape and a series of tabs releasably and adhesively mounted on the mounting tape, the mounting tape extending from the supply reel to an applicator containing perfume or deodorant and being arranged to apply a coating of the perfume or deodorant to the top surface of the tabs, said applicator being in continuous bearing contact with the mounting tape, the mounting tape extending from the applicator to a discharge means arranged such that the mounting tape is sharply redirected adjacent the discharge opening, the mounting tape extending from the discharge opening to a take-up reel, the arrangement being such that in use as the mounting tape is sharply redirected adjacent the discharge opening, one of said tabs having its top surface coated with perfume or deodorant is released from the mounting tape and is discharged from the discharge opening, the mounting tape from which tabs have been released being taken up by the take-up reel.

2. A dispenser device according to claim 1 wherein the take-up reel is provided with and rotable by a thumb wheel projecting through an aperture in the housing.

3. A dispenser device according to claim 1 wherein the discharge means comprises a discharge member positioned at the discharge opening, the mounting tape being redirected in use over the discharge member through an angle of at least 160 degrees.

4. A dispenser device according to claim 1 wherein the applicator comprises a porous reservoir member impregnated with said perfume or deodorant and positioned to wipe the top surface of the tabs on the mounting tape.

5. A dispenser device according to claim 4 including a backstop member positioned on the opposite side of the mounting tape to the porous reservoir member, providing a support for the mounting tape as it engages the porous reservoir member.

6. A dispenser device according to claim 1 wherein the applicator is formed as a replaceable unit having engaging means making a snap-fit within the walls of the housing.

* * * * *